United States Patent [19]

Ismail et al.

[11] Patent Number: 4,956,301

[45] Date of Patent: Sep. 11, 1990

[54] TEST DEVICE AND METHOD OF ASSAYING FOR FRUCTOSAMINES

[75] Inventors: Ibrahim A. Ismail, South Bend; David W. Michaels, Elkhart, both of Ind.

[73] Assignee: Miles Inc., Elkhart, Ind.

[21] Appl. No.: 430,328

[22] Filed: Nov. 2, 1989

[51] Int. Cl.$^5$ .................... G01N 33/00; G01N 33/48; G01N 33/49

[52] U.S. Cl. .......................... 436/87; 436/95; 436/111; 436/169; 436/903; 436/904; 422/56

[58] Field of Search ............ 436/87, 169, 111, 8, 436/14, 15, 16, 34, 63, 67, 88, 95, 164, 903, 904; 422/56, 57, 58

[56] References Cited

U.S. PATENT DOCUMENTS

| | | | |
|---|---|---|---|
| 2,981,606 | 4/1961 | Keston | 436/95 |
| 3,791,988 | 2/1974 | Josef et al. | 422/56 |
| 3,920,580 | 11/1975 | Mast | 436/14 |
| 4,211,845 | 6/1980 | Genshaw et al. | 436/95 |
| 4,336,330 | 6/1982 | Bauer | 422/56 |
| 4,371,374 | 2/1983 | Cerami et al. | 436/87 |
| 4,642,295 | 2/1987 | Baker | 436/87 |
| 4,645,742 | 2/1987 | Baker | 436/87 |
| 4,748,114 | 5/1988 | Kallies et al. | 422/56 |

OTHER PUBLICATIONS

"Fructosamine: A New Approach to the Estimation of Serum Glycoprotein, an Index of Diabetic Control," Johnson et al., *Clin. Chim. Acta*, 127(1), 1983, pp. 87–95.

*Primary Examiner*—Robert J. Warden
*Assistant Examiner*—Thalia P. Vassilatos
*Attorney, Agent, or Firm*—Roger N. Coe

[57] ABSTRACT

A new and improved test device and method of determining the presence and concentration of fructosamines in a test sample. The test device includes a test pad comprising a carrier matrix incorporating an indicator reagent composition capable of interacting with fructosamines to produce a detectable or measurable response. The carrier matrix of the device includes a bibulous matrix, such as filter paper, or a nonbibulous matrix, such as a polymeric film. In addition, a new and improved indicator reagent composition comprising a dye, such as tetrazolium violet; a suitable buffer; and an accelerator compound is incorporated into the carrier matrix to provide a test pad demonstrating sufficient color resolution and having sufficient sensitivity to fructosamines in a test sample. Therefore, a fast, more accurate and trustworthy fructosamine assay of a liquid test sample, such as whole blood or serum, is achieved. The improved method of determining the presence or concentration of fructosamines in a liquid test sample is especially useful in the diagnosis and treatment of diabetes mellitus.

39 Claims, 3 Drawing Sheets

TEST DEVICE AND METHOD OF ASSAYING FOR FRUCTOSAMINES

FIELD OF THE INVENTION

The present invention relates to a composition, test device and method of assaying a liquid test sample for the presence or concentration of fructosamines. More particularly, the present invention relates to a new and improved method and device for assaying a liquid, such as whole blood or serum, for fructosamines by utilizing a device having an indicator reagent composition incorporated into a carrier matrix, such that a detectable or measureable response occurs upon contact of the indicator reagent composition with a fructosamine-containing liquid test sample. The indicator reagent composition provides sufficient fructosamine sensitivity and sufficient color resolution between different fructosamine concentrations in order to quickly and more accurately detect or measure, either visually or by instrument, the fructosamine content of the liquid test sample. In addition, the present invention relates to using an indicator reagent composition, incorporated into a carrier matrix, in a method to determine the presence or concentration of fructosamines in a test sample by a dry phase, test strip assay procedure.

BACKGROUND OF THE INVENTION AND PRIOR ART

Individuals suffering from diabetes mellitus have an abnormally high blood sugar level because the pancreas does not secrete sufficient amounts of the hormone insulin into the bloodstream to regulate carbohydrate metabolism. If an abnormally high blood sugar level, i.e. a hyperglycemic condition, is allowed to continue for prolonged periods, the individual will suffer from the chronic complications of diabetes, including retinopathy, nephropathy, neuropathy and artherosclerosis.

Accordingly, it is important that a hyperglycemic condition, or excess sugar in the blood, be controlled in order to prevent, or ameliorate, the chronic complications of diabetes. Therefore, in order to prevent the chronic complications of diabetes, the blood glucose level of a diabetic individual is maintained as closely as possible to the blood glucose level found in healthy individuals. Usually, blood glucose levels are maintained by periodically injecting insulin into the individual in order to provide the hormone necessary for glucose metabolism.

As a result, reliable test methods are needed in order for the individual, or a physician, to determine blood sugar levels such that a physiologic abnormality can be properly treated, or diagnosed, and such that a proper treatment schedule is instituted and maintained. Unfortunately, many of the prior art methods of determining the amount of glucose in the blood are unsatisfactory either because the method requires patient cooperation, such as fractional urine collections by the individual at home, or because the method is cumbersome and unreliable, such as 24 hour urinary glucose excretion. In addition, blood glucose levels fluctuate considerably throughout the day because of the influences of diet, physical activity, and medical treatment. Therefore, random blood glucose assays are an inadequate and/or misleading indicia of blood sugar control.

Consequently, in attempting to control an established case of diabetes mellitus, an accurate assay of the actual, and not the apparent, long-term blood glucose level is necessary. An early prior art method measured the amount of glycosylated hemoglobin in the blood as an indicator of blood sugar, or glucose, concentration. This assay has proved useful in monitoring the control of diabetes mellitus, but the assay is expensive and assay results are relatively nonreproducable. Therefore, the need for a more reliable assay for glucose concentration has led to the present investigation, wherein a fast and accurate fructosamine assay can be correlated to the glucose concentration of the liquid test sample.

Fructosamines are a product of the interaction of serum glucose with serum proteins over a period of days to weeks. An assay for fructosamines overcomes some of the disadvantages of the assay for glycosylated hemoglobin because fructosamines are stable, and fructosamine concentration does not change with short term fluctuations in blood glucose levels. As will be demonstrated more fully hereinafter, the fructosamine assay of the present invention also is economical, accurate, and reproducible, and can be performed on one or two drops of test sample.

It is known that proteins, such as those present in blood serum, react with glucose either in vivo or in vitro, under non-enzymatic conditions, to produce glycated proteins, also known as fructosamines or ketoamines. In addition, the fructosamine concentration of a test sample can be correlated to diabetic glycemic control, especially relating to the 3 to 6 weeks prior to testing. Furthermore, the amount of fructosamine present in the blood also has been found to correlate with fasting plasma glucose and hemoglobin $A_{Ic}$ (Hb$A_{Ic}$) in individuals suffering from diabetes. In addition, both the time of taking the liquid test sample and the relation of the test sample to diet are unimportant.

The glycosylation of proteins to form fructosamines is a non-enzymatic reaction. The extent of the reaction is directly dependent upon the glucose concentration of the blood. Consequently, diabetics usually have an elevated fructosamine concentration in the blood compared to a healthy individual. Therefore, the concentration of glycated serum proteins or glycated hemoglobin has been used as an indicator of a glycemic condition. In particular, an assay for fructosamines provides a method of diagnosing for diabetes mellitus and of monitoring diabetic control measures because fructosamine concentration reflects an average of serum glucose levels over a period of time.

It is known that blood glucose reacts continuously with proteins. The glucose binds to an amino group of a protein to form a Schiff base, i.e., an aldimine, that undergoes a molecular rearrangement to form a stable ketoamine In the art, such ketoamines are generically termed "fructosamines". Therefore, in accordance with the method of the present invention, blood sugar concentrations are determined indirectly by assaying for fructosamines.

The formation of fructosamines is demonstrated in the following chemistry scheme The blood proteins are glycated in vivo by a non-enzymatic reaction between glucose and available amino groups of blood proteins.

Glucose      Glycosylamine      Fructosamine The degree of protein glycosylation is directly proportional to blood glucose concentration. In general, the fructosamine concentration in the blood reflects an average glucose concentration in the blood over a period of time. Therefore, diabetic individuals have a higher fructosamine concentration in the blood than unaffected individuals. Then, under alkaline conditions, the fructosamines that form in the blood are converted to eneaminols. The eneaminol form of fructosamine is a chemically active reducing substance that reacts with a suitable indicator dye to give a color transition that can be measured and compared with a standard to give an indication of the glucose concentration in blood samples This correlation to glucose concentration is possible even though the glucose remains interacted with or associated with the protein in the blood and has undergone a molecular rearrangement to form a fructosamine.

Fructosamine      Eneaminol
(Ketoamines)      (Reducing agent)

Fructosamine concentration in the blood is an indicator of a diabetic condition, and is an indicator of diabetic control measures that are dependent on the patient's diet, activity and/or treatment. The major clinical use of a fructosamine assay is the diagnosis of diabetes, the regulation of treatment for known diabetics and the assessment of new diabetes treatments. A rapid and accurate fructosamine assay also can be used to screen populations with an increased risk of developing diabetes, such as pregnant women, the obese, and the ethnic groups with a known predisposition to diabetes. Therefore, if a rapid and accurate fructosamine assay of blood samples were available, the assay could assess glycemic control, therapeutic regimen and patient compliance over extended time periods in order to avoid the complications of diabetes associated with hyperglycemia. Accordingly, the availability of a trustworthy fructosamine plasma or serum diagnostic assay would compliment the battery of assays, such as plasma glucose and $HbA_{Ic}$, presently performed by physicians in the diagnosis of diabetes and in the care and treatment of diabetics.

Baker, in U.S. Pat. Nos. 4,642,295 and 4,645,742, and in European patent application No. 82307051.1, discloses a method of determining fructosamine levels in blood samples based upon the above-described chemical scheme The method disclosed by Baker is a wet phase assay, wherein the blood serum must be separated from the highly-colored red blood cells. After separation of the serum from the blood cells, the serum sample is buffered to a pH of between 10 and 11 and a coloring agent, nitroblue tetrazolium, is added. The resulting mixture is allowed to stand for 10 to 15 minutes, then any color change resulting from a reaction between the nitroblue tetrazolium and the eneaminol form of the frustosamine is measured. In order for the assay to proceed in a relatively rapid fashion, the buffered serum sample containing the nitroblue tetrazolium is maintained at 37° C., or 98.6° F., throughout the assay. However, the method of Baker suffers from several practical limitations such as the inconvenience of a wet phase assay; the need for a relatively large blood sample volume of about 2 ml; the elevated temperature required to effect the reaction; the length of time to complete the assay; and the need to separate blood serum from blood cells. These drawbacks make laboratory assays for fructosamines time-consuming and burdensome, and such practical limitations are especially disadvantageous for an individual desiring to conduct a fructosamine assay at home.

German Patent No. DE 36 20 817 describes a wet phase chromogenic assay for fructosamines that first eliminates the interfering components in the serum by treating the serum with a lipase and either an oxidase, a peroxidase or a catalase, at a neutral pH. This method eliminates any non-specific reducing components and turbidity-forming components from the serum. Then, the serum is assayed for fructosamine concentration at a pH of 10 to 11. In contrast, the composition and method of the present invention is a dry phase assay for fructosamines that is essentially unaffected by the non-specific reducing components. Furthermore, the present invention does not require the time-consuming manipulative steps of adjusting the pH to a value of 10 to 11, then adding the indicator dye.

Japanese Kokai Patent No. Sho 60 (1985)-227171 discloses a method of assaying for blood sugar by determining the concentration of glucose combined with hemoglobin. The Japanese patent discloses a wet assay method wherein a hemolyzed blood sample, preferably plasma-free, is mixed with nitroblue tetrazolium in a composition that first converts the hemoglobin from a tetramer to a monomer. Then, the glucose bound to the hemoglobin (as fructosamine) is determined spectrophotometrically. The Japanese patent does not teach or suggest using a dry phase test strip to assay blood or serum for glucose concentration by determining the amount of glucose bound to a protein in the fructosamine form. Furthermore, like the other prior art fructosamine assays, the Japanese method is a wet assay method requiring several manipulative steps, such as preferably using separated and washed blood cells to avoid assay interference attributed to fructosamines arising from glucose bound to proteins.

Therefore, the need exists for a rapid, accurate fructosamine assay of blood samples. The fructosamine assay should be an easy-to-perform assay, either at home or in a medical office, in order to rapidly determine if a glycemic condition exists and to rapidly determine the efficacy of the prescribed medical treatment for diabetes. Accordingly, investigators have attempted, and failed until the present invention, to provide a fructosamine assay in the dry phase test strip format. At present, no commercial fructosamine test strips are available, and no fructosamine test strips are known to be disclosed in prior art patents or publications.

Consequently, in order to determine if an individual is hyperglycemic, i.e., has an excess amount of sugar in the blood, or is hypoglycemic, i.e., has a lack of sugar in the blood, and in order to monitor the course of a medical treatment to determine the effectiveness of that treatment, a simple, accurate and inexpensive assay that correlates to the amount of sugar in the blood is needed. Although semiquantitive, colorimetric reagent test strip assays are available for the determination of sugar content in a test sample, until the method and device of the present invention no dry phase colorimetric test strips were available to indirectly assay for blood sugar content by measuring fructosamine content.

In general, a colorimetric reagent test strip utilizes the ability of the analyte of interest to interact with certain reagents present in the test pad of the test strip and to ultimately alter the color of an indicator present in the test pad. Some colorimetric test strips used in blood assays have a single test area consisting of a small square pad of a carrier matrix impregnated with the reagents necessary to interact with the analyte of interest to produce a detectable response. Other colorimetric test strips are multideterminant reagent strips that include one test area for the assay of a particular analyte, and further include several additional test areas on the same strip to permit the simultaneous assay of other blood constituents. For both types of colorimetric test strips, the assay for a particular analyte is performed by simply dipping the colorimetric test strip into a fresh whole blood, or blood serum, sample, then comparing the resulting color of the test area of the test strip to a standardized color chart provided on the colorimetric test strip bottle.

However, until the test device of the present invention, no dry phase test strips were available to allow an accurate determination of fructosamine content in blood. Therefore, it would be extremely advantageous to have a simple, accurate and trustworthy method of assaying blood or blood serum for fructosamine content that allows visual differentiation of fructosamine levels in the range of from about 0.5 mMol/L to about 6 mMol/L, and especially in the range of from about 1 mMol/L to about 4 mMol/L. The fructosamine concentration in the blood then can be correlated to the amount of glucose in the blood to provide an indirect blood sugar measurement. By providing an accurate method of determining the fructosamine concentration in an easy to use form, like a dip-and-read test strip, the blood assay can be performed by laboratory personnel to afford immediate test results such that correct medical treatment can be commenced immediately. In addition, the test strip method can be performed by the patient at home to more precisely monitor fructosamine levels, and therefore sugar levels, in the blood as a measure of the success of the medical treatment the patient is undergoing.

As will be described more fully hereinafter, the method of the present invention allows the fast, accurate and trustworthy fructosamine assay of blood by utilizing a test strip that includes an indicator reagent composition. The indicator reagent composition of the present invention provides sufficient visual color resolution between different fructosamine concentrations, and therefore the assay has sufficient sensitivity to allow fructosamine concentrations to be accurately determined. All prior art assay techniques for fructosamines involve wet assay methods that are time consuming and are not amenable for use by the patient at home.

Therefore, incorporating a highly sensitive indicator reagent composition into a suitable carrier matrix provides a test pad for use in a dry phase test strip of the present invention that allows the rapid, room temperature determination of fructosamine levels in blood or serum. The detection and measurement of fructosamines in blood can be correlated to the amount of sugar in the blood such that a correct diagnosis for glycemia can be made, and such that correct medical treatment can be implemented, monitored and maintained. In addition, because the fructosamine assay is in a dip-and-read format, the assay provides for the easy and economical, qualitative or quantitative determination of fructosamines in blood or other liquid test samples.

Any colorimetric method of assaying for fructosamine in blood or other liquid test samples must yield accurate, trustworthy and reproducible results by utilizing a reagent composition that undergoes a color transition as a result of an interaction with fructosamines, and not as a result of a competing chemical or physical interaction, such as a pH change or a preferential interaction with a test sample component other than fructosamines. Additionally, the method and composition utilized in the assay for fructosamines should not adversely affect or interfere with the other test reagent pads that are present on multiple test pad strips.

Prior to the present invention, no known method of assaying blood or other liquid test samples for fructosamines included an indicator reagent composition incorporated into a suitable carrier matrix to provide sufficient color resolution of the assay and sufficient sensitivity of the assay to fructosamine concentrations, such that an accurate and trustworthy fructosamine assay is available for fructosamine concentrations ranging from about 0.5 mMol/L to about 6 mMol/L, and especially from about 1 mMol/L to about 4 mMol/L. Furthermore, until the method of the present invention, no dry phase test strip procedures were available to assay for the fructosamine concentration in blood or other liquid test samples. However, surprisingly and unexpectedly, the method of the present invention permits the dry phase test strip assay of blood and other liquid test samples for fructosamines, in order to diagnose a glycemic condition and to monitor treatments for glycemic conditions.

In contrast to the prior art assay procedures, the method of the present invention provides sufficient sensitivity in the detection and measurement of fructosamines in a liquid test sample by utilizing a dry phase test strip comprising a test pad including a carrier matrix incorporating an indicator reagent composition. By using the method and device of the present invention, fructosamine levels from about 0.5 mMol/L to about 6 mMol/L, and especially from about 1 mMol/L to about 4 mMol/L, can be determined accurately. Hence, in accordance with the method of the present invention, new and unexpected results are achieved in the dry phase reagent strip assay of blood and other liquid test samples for fructosamines, by utilizing an indicator reagent composition incorporated into a suitable carrier matrix.

SUMMARY OF THE INVENTION

In brief, the present invention is directed to a new and improved composition, test device, and method of determining the presence or concentration of a component in a test sample. The test device includes a carrier matrix incorporating a reactant composition capable of interacting with a test sample component to produce a detectable response. For home use, the reactant composition produces a visually detectable response. For laboratory use, the reactant composition produces a response that is detectable visually or by instrument. The carrier matrix of the device of the present invention comprises such bibulous porous materials as filter paper, or such nonbibulous porous materials as a permeable strip, membrane or layer of a polymer, like a polyurethane or a polyacrylamide. A reactant composition can be homogeneously incorporated into the carrier matrix, and the carrier matrix then holds the reactant composition homogeneously throughout the carrier matrix in a known concentration while maintaining carrier matrix penetrability of the predetermined component.

More particularly, the present invention is directed to a method of assaying blood, serum or other liquid test samples for fructosamines by utilizing a new and improved indicator reagent composition. It has been demonstrated that a composition comprising an indicator dye, a buffer, and a reaction accelerator is capable of undergoing detectable and measurable color transitions in the presence of fructosamines to afford improved color resolution and increased sensitivity to fructosamine concentration in a liquid test sample. In accordance with an important feature of the present invention, the qualitative or quantitative determination of fructosamine levels between about 0.5 mMol/L and about 6 mMol/L, and especially between about 1 mMol/L and about 4 mMol/L, in blood and other liquid test samples is accomplished. By utilizing the indicator reagent composition of the present invention in dry phase clinical test methods, the qualitative or quantitative determination of fructosamines in blood, serum or other test samples can be more accurately determined because the improved color resolution afforded by the combination of the dye, the buffer and the reaction accelerator compound increases the sensitivity of the method to the fructosamine concentration of the liquid test sample.

Therefore, it is an object of the present invention to provide a new and improved method and test device for determining the relative concentration of a chemical compound in a liquid.

Another object of the present invention is to provide a simple, accurate and reproducible method of assaying blood, serum or other liquid test samples for fructosamines.

Another object of the present invention is to provide a method of assaying blood, serum or other liquid test samples that provides improved visual color resolution and increased sensitivity to fructosamine concentrations.

Yet another object of the present invention is to provide a method of assaying blood, serum or other liquid test samples that is sensitive to fructosamine concentrations of greater than about 0.5 mMol/L and that quantitatively discriminates between fructosamine levels of from about 0.5 mMol/L to about 6 mMol/L, and especially from about 1 mMol/L to about 4 mMol/L.

Another object of the present invention is to provide a method of assaying blood, serum or other test liquids for fructosamines that utilizes an indicator reagent composition.

Another object of the present invention is to provide a method of assaying blood, serum or other test liquids by utilizing an indicator reagent composition that can interact with fructosamines and undergo a detectable and measurable color transition to establish the presence or concentration of fructosamines in the test sample.

Another object of the present invention is to provide a method of assaying blood, serum or other test samples for the presence or concentration of fructosamines in order to detect a glycemic condition, such as diabetes mellitus, in individuals and/or to monitor the treatment of an individual having a glycemic condition.

Another object of the present invention is to provide a method of assaying for fructosamines by incorporating the indicator reagent composition into a dry phase detection device comprising a carrier matrix having a porosity sufficient to allow penetration by the test sample and contact of the test sample with the indicator reagent composition.

Another object of the present invention is to provide an indicator reagent composition that, when appropriately buffered, can interact with fructosamines and undergo a visually or instrumentally differentiable color transition to allow the quantitative determination of the concentration of fructosamines in the blood, serum or other liquid samples at levels between about 0.5 mMol/L and about 6 mMol/L, and especially between about 1 mMol/L and about 4 mMol/L.

Another object of the present invention is to provide an indicator reagent composition comprising an indicator dye, a buffer and a reaction accelerator compound that, when incorporated into a suitable carrier matrix, can be used to assay for the fructosamine concentration of a liquid test sample.

Another object of the present invention is to provide a new and improved test device for the quantitative analysis of fructosamines.

Another object of the present invention is to provide a new and improved fructosamine interactive test device for interaction with fructosamines in a test fluid to produce a visible change, such as a change in color, of the test device, indicative of the fructosamine concentration in the test fluid.

Another object of the present invention is to provide a reagent test strip including a test pad comprising a carrier matrix capable of homogeneously incorporating an indicator reagent composition that interacts with the fructosamine concentration of a test sample.

Another object of the present invention is to provide a new and improved test device and method of manufacturing the test device for sensing the presence of a chemical compound in a liquid, wherein the chemical compound is capable of permeating a carrier matrix and is capable of interacting with an indicator reagent composition incorporated into the carrier matrix to produce a detectable and measurable response.

A still further object of the present invention is to provide a new and improved dry phase test strip capable of incorporating an indicator reagent composition into the carrier matrix to achieve a test strip of new and unexpected precision in fructosamine response.

Another object of the present invention is to provide a method of detecting diabetes mellitus in an individual by assaying the blood of the individual for fructosamines with a test device including a test pad comprising a carrier matrix homogeneously impregnated with an indicator reagent composition comprising an indicator dye, like tetrazolium violet; a buffer; and a reaction accelerator compound.

BRIEF DESCRIPTION OF THE DRAWINGS

The above and other objects, advantages and novel features of the present invention will become apparent from the following detailed description of the preferred embodiments of the invention illustrated in the accompanying figures showing the enhanced color resolution of the color transition of the dry phase test strips and the increased sensitivity to fructosamines, thereby permitting accurate quantitative analyte determinations and more accurate diagnoses.

DETAILED DESCRIPTION OF THE INVENTION

In accordance with the method of the present invention, the qualitative or quantitative assay for fructosamines in blood, serum and other liquid test samples is accomplished by utilizing a dry phase test strip including a test pad comprising an indicator reagent composition homogeneously incorporated into a suitable carrier matrix. By employing an indicator reagent composition comprising a suitable indicator dye, a buffer and a reaction accelerator compound, the assay provides sufficient sensitivity to fructosamines and sufficient color resolution between different fructosamine concentrations to allow the accurate determination of fructosamine concentration in a liquid test sample. The color resolution and assay sensitivity to fructosamines afforded by the method of the present invention is especially useful in blood assays, such as in the diagnosis of a glycemic condition, like diabetes mellitus, or in the monitoring of the treatment of a glycemic condition.

The fructosamine concentration in a blood sample is an indicator of how effectively an individual metabolizes sugar. Therefore, a reliable fructosamine assay can be used either by a physician to help diagnose a glycemic condition, like diabetes mellitus, or by a physician or an individual at home to help monitor the course of a medical treatment for a glycemic condition. If the individual suffers from diabetes mellitus, an accurate assay for fructosamines amines can monitor patient compliance, quality of care, and the efficacy of insulin therapy. Therefore, in accordance with the present invention, the fructosamine concentration of blood can be measured at sufficient intervals, either at home or in a medical office, to accurately and reliably detect diabetes mellitus or to detect any improvement or deterioration in diabetic control.

In general, fructosamines arise in blood samples through the glycosylation of proteins present in the blood serum. Because albumin is the predominant serum protein, i.e., about 55% of the serum protein, the fructosamine present in greatest concentration is the fructosamine resulting from the interaction between glucose and albumin. Therefore, the vast majority of individuals, except those individuals having an exceptionally low albumin concentration in the blood, have a detectable fructosamine concentration in their blood. Consequently, because individuals that suffer from diabetes mellitus have abnormally high blood sugar, or glucose, levels, these individuals also have abnormally high fructosamine levels in their blood. As a result, fructosamine concentration in the blood can be used as an indicator of a diabetic condition, and of the severity of the diabetic condition. Similarly, the assay for fructosamines can be useful as a screening test to detect individuals with diabetes mellitus In general, a known diabetic has a fructosamine concentration in the blood of about 2 mMol/L, such as from about 1.7 mMol/L to about 2.6 mMol/L. Likewise, pregnant females often exhibit gestational diabetes, wherein the fructosamine concentration in the blood can approach about 2 mMol/L, and usually is in the range of from about 1.7 mMol/L to about 1.9 mMol/L. Therefore, for an individual exhibiting normal glucose levels, the fructosamine level in the blood is usually below about 1.8 mMol/L. Fructosamine levels in the blood at or above a level of 1.8 mMol/L indicate a possible diabetic condition that should be more carefully examined by such assays as fasting plasma glucose and hemoglobin $A_{Ic}$. Similarly, for known diabetics, fructosamine levels in the blood above about 1.8 mMol/L indicate that the present treatment for diabetes mellitus is insufficient and may have to be altered.

Therefore, it is important that an assay for fructosamines is capable of differentiating between fructosamine levels ranging from about 0.5 mMol/L to about 6 mMol/L, and especially from about 1 mMol/L to about 4 mMol/L. Differentiating between fructosamine concentration levels is clinically important in the art because a range of from about 1.0 mMol/L to about 1.8 mMol/L is considered as the normal fructosamine level for a healthy individual. Therefore a fructosamine level of from about 1.8 mMol/L and above is one indication of a potential diabetic condition that can cause acute reactions and chronic complications in the individual. Accordingly, the method and composition of the present invention afford sufficient color resolution and sufficient sensitivity to differentiate between blood fructosamine concentrations of from about 0.5 mMol/L to about 6 mMol/L. Therefore, an accurate and reliable assay for fructosamines is achieved such that abnormally high fructosamine assay levels are definitely indicative of an abnormal physiological state that must be investigated further Therefore, as will be discussed more fully hereinafter, a method and device is available to accurately assay for the fructosamine content in blood or serum by a dry phase test strip procedure. Furthermore, it will become apparent that in addition to assaying blood or serum, the method and device of the present invention also can be used to determine the presence or concentration of fructosamines in other liquid test samples containing a sugar and a protein. In particular, the method and device of the present invention provide a fast and reliable assay for fructosamines, performed at home or in a medical office, to assist in the diagnosis of diabetes mellitus or to assist in monitoring the treatment of diabetes mellitus.

Surprisingly and unexpectedly, it has been found that combining a suitable indicator dye with a suitable buffer and a reaction accelerator provides an indicator reagent composition that interacts with fructosamines at room temperature. The indicator reagent composition demonstrates sufficient color resolution between, and sufficient sensitivity to, fructosamine concentrations to permit the assay for the presence or concentration of fructosamines in a test sample. The colorimetric technique using the indicator reagent composition provides an accurate, trustworthy and clinically-significant assay for fructosamines. Presently, only a liquid phase assay, performed at elevated temperatures, has been suggested as a viable assay for the fructosamine levels in blood or serum. Surprisingly and unexpectedly, the method and composition of the present invention provide a dry phase test strip assay, performable at room temperature, to determine the presence or concentration of fructosamines in a liquid test sample.

The dye used in the wet phase assay for fructosamine, as disclosed by Baker in U.S. Pat. Nos. 4,645,742 and 4,642,295 and in European patent application No. 82307051.1, interacts with the chemically-reactive eneaminol form of the fructosamine. When maintained at the proper, constant pH, the dye undergoes a chemical change due to an interaction with the fructosamine, and a color transition results. The intensity of the color transition then is determined, either visually or by instrument, to detect and measure the amount of fructosamines in the test sample. The Baker disclosures describe using a tetrazolium salt, such as nitroblue tetrazolium, that interacts with a fructosamine to form a highly colored formazan dye having a broad absorbance peak at about 535 nanometers (nm). The intensity of the resulting purple color is correlated to the amount of fructosamines in the sample; and the amount of fructosamines in the sample then can be related to the amount of glucose in the sample.

The Baker patents basically describe the present-day wet phase assay for fructosamine content in serum. This assay, performed at elevated temperatures, utilizes an indicator dye that undergoes a color transition in the presence of a fructosamine that is in its reactive eneaminol form. Therefore, to assure that the fructosamine is in the active eneaminol form, the wet phase assay is maintained at a strongly alkaline pH of 10 or above, and preferably at a pH of between 10 and 11. A sufficient buffering of the indicator dye essentially insures that the dye changes color due to an interaction with fructosamine rather than due to a pH change occurring upon contact with the test sample.

In accordance with an important feature of the present invention, it has been demonstrated that the judicious selection of an indicator dye, properly buffered at a suitable pH, provides an accurate and trustworthy assay for fructosamine content in liquid samples. Furthermore, surprisingly and unexpectedly, by incorporating a reaction accelerator with the indicator dye and the buffer into a carrier matrix, a test pad is provided for use in a dry phase test strip to assay for fructosamine concentration in blood at room temperature. Therefore, a method of fast, accurate, reproducible and trustworthy fructosamine assays, performable at home or in the laboratory, to yield essentially immediate assay results, is achieved It should be noted that the assay does not measure free glucose in the blood, or glucose in the reversible glycosylamine form. The assay does however measure glucose in the stable fructosamine form. This assay for fructosamines then can be correlated to the concentration of free glucose in the blood.

Therefore, in accordance with an important feature of the present invention, the indicator reagent composition must include a suitable indicator dye. In contrast to the prior art, the incorporation of an indicator dye, a buffer and a reaction accelerator compound into a carrier matrix provides a test pad for a dry phase fructosamine assay that exhibits sufficient color resolution and differentiation, both visually and instrumentally, of the color transition occurring upon interaction of the indicator dye with the fructosamine. Accordingly, the facility of the fructosamine assay is increased.

The method of the present invention utilizes the previously discussed interaction between the eneaminol form of the fructosamine and the indicator dye. In general, any indicator dye can be utilized in the method of the present invention provided that the indicator dye can interact with fructosamines to undergo a detectable or measurable color transition in response to the fructosamine interaction. The indicator dye utilized in the indicator reagent composition preferentially interacts with fructosamines as opposed to any competing chemical or physical interactions with non-fructosamine components in the liquid test sample. Any appreciable competing interactions with non-fructosamine components could lead to false and erroneous assays concerning the presence and amount of fructosamine in the test sample unless appropriate corrections are made. For example, the proper buffering of the indicator dye precludes the possibility of a color transition occurring because of a pH change and also insures that the fructosamines are present in the reactive eneaminol form.

It has been found that any indicator dye that is capable of interacting with fructosamines to undergo a sufficient color transition in a sufficiently alkaline pH range can be used in the method of the present invention. Depending upon several chemical and physical parameters, such as an ability to interact with fructosamines, intensity of the color transition and chemical compatibilty between the components of the indicator reagent composition, the exact amount of the indicator dye in the indicator reagent composition can be determined by those skilled in the art of designing test kits in order to produce an assay for fructosamines having maximum visual color resolution and maximum sensitivity. The indicator dyes utilized in the indicator reagent composition of the present invention are known and can be prepared by methods well known to persons in the art. Furthermore, several indicator dyes that are useful in the method of the present invention are well known indicator dyes that are presently available commercially.

An indicator dye as described above is utilized in an indicator reagent composition in an improved method to determine the presence or the concentration of fructosamines in blood serum or other liquid test samples. It has been demonstrated that the indicator reagent composition of the present invention interacts with fructosamines to produce a differentiable and measurable color transition, either visually or by instrument, due to the interaction of the indicator dye and the fructosamine. However, in addition to the indicator dye, the indicator reagent composition of the present invention also requires a sufficient amount of a proper buffer, such that the dye does not change color as a result of a pH shift, but changes color upon contact and interaction with fructosamines. Furthermore, the buffer insures that the pH remains sufficiently high such that the fructosamine is present in the reactive eneaminol form for interaction with the indicator dye to accurately establish the presence or concentration of fructosamines in the test sample.

Further, it has been demonstrated that any of various known types of buffers can be used in the indicator reagent composition of the present invention as long as the buffer provides a sufficiently high pH such that the fructosamines are present in the eneaminol form. The function of the buffer is to maintain the indicator reagent composition at a substantially alkaline pH to produce the desired color transition in the indicator dye because of the presence of fructosamines. As a result, the amount of buffer incorporated into the indicator reagent composition depends upon the nature of the test sample and the nature of the indicator dye. The quantity of buffer usually is within the range of from about 0.1 molar (M) and about 1 molar, although in particular cases the amount of buffer can be above or below this range. The particular buffer used in the indicator reagent composition depends upon, and varies with, the indicator dye incorporated into the indicator reagent composition. However, it has been found that for optimum results, the pH of the reagent composition generally is maintained at a pH value of between about 11 and about 13. To achieve the full advantage of the present invention, the pH is maintained at a pH value of between 11 and 12.5.

The indicator reagent composition of the present invention also includes a reaction accelerator compound such that the interaction between the fructosamines and the indicator dye that produces the detectable color transition can occur at room temperature. The prior art wet phase fructosamine assay disclosed by Baker required elevated temperatures, like 37° C., i.e. 98.6° F., in order for the fructosamine-indicator dye interaction to proceed at a reasonable rate. Surprisingly and unexpectedly, it has been found that incorporating an indicator reagent composition, including a reaction accelerator compound, into a carrier matrix provides a test pad to assay for fructosamines at room temperature.

In addition, optional ingredients that do not materially alter the nature or the function of the indicator dye, the buffer or the reaction accelerator compound, and that do not interfere with the fructosamine assay, also can be included in the indicator reagent composition. Other such non-essential ingredients include nonreactive background dyes, polymers, plasticizers, wetting agents and stabilizers.

Therefore, in accordance with the present invention, it is possible to perform an accurate and trustworthy fructosamine assay at ambient temperature, on a small test sample volume, with a dry phase test strip, wherein the assay results are available within a few minutes. Previous assays for fructosamines required relatively large test samples, elevated temperatures, longer reaction times, and the more burdensome wet phase assay techniques that are not amenable to home use. However, the composition and method of the present invention provide a sensitive, economical and easy-to-use fructosamine assay, in a dry phase test strip format, that yields fast and accurate assay results.

Upon contact with the blood, serum or other liquid test sample, a color transition of the indicator reagent composition demonstrates the presence of fructosamines. Furthermore, the intensity and degree of the color transition is used to determine the concentration of fructosamines in the test sample by comparing or correlating the color produced by the test sample to colors produced by solutions having a known concentration of fructosamines. In accordance with an important feature of the present invention, it has been demonstrated that the indicator reagent composition provides a sufficiently resolved and differentiated color transition such that the amount of fructosamine in the test sample can be measured and accurately determined without the use of color-measuring instruments, such as spectrophotometers or colorimeters. However, if desired, such color-measuring instruments can be used to measure the difference in color degree and intensity between the test sample and a solution of known fructosamine concentration.

Accordingly, an assay for fructosamines that utilizes a suitable indicator reagent composition incorporated into a suitable carrier matrix improves the accuracy and reliability of the assay and also increases physician confidence in the assay and any resulting diagnosis. Additionally, because of the number of assays being performed at home by the untrained patient, as opposed to trained physicians or technicians in the laboratory, it is important to provide accurate and reliable quantitative assay methods for fructosamine content in the blood, serum or other liquid test sample.

In accordance with an important feature of the present invention, indicator dyes that can be used in the indicator reagent composition of the present invention include dyes that are reduced by sugars and as a result undergo a color transition. For example, the compound triphenyltetrazolium chloride, depicted as structural formula I, is essentially colorless when dissolved in water. However, the compound of structural formula I is reduced by sugars to form a water-insoluble triphenylformazan. The triphenylformazan compound is a deep red pigment, and therefore the degree of color formation can be correlated to the amount of fructosamines in the liquid test sample. Similarly, other tetrazolium indicators, such as tetrazolium violet, blue tetrazolium and 3-(4,5-dimethyl-2-thiazolyl)-2,5-diphenyl-2H-tetrazolium bromide (MTT), or combinations thereof, also were found to be useful indicator dyes. However, it was found that the preferred indicator dye of the prior art, nitroblue tetrazolium, could not be used in the method of the present invention because nitroblue tetrazolium is not stable under the pH conditions of the indicator reagent composition used in the present invention.

I

Other indicator dyes useful in the present invention, in addition to or in combination with suitable tetrazolium dyes, include 2,6-dichlorophenol indophenol dyes. However, the 2,6-dichlorophenol indophenol dyes are colored in the non-reduced state, therefore imparting a background color to the carrier matrix of the test pad. Accordingly, the use of an indicator dye that is colored in the non-reduced state may result in a loss of assay sensitivity due to an interfering background color. An additional reducible dye that can be used in the method and composition of the present invention is p-dimethylaminobenzaldehyde coupled with acetylacetone. In addition, the aroylhydrazines, like 4-hydroxybenzoylhydrazine, 2-furoylhydrazine, nicotinoyl hydrazine, isonictinoyl hydrazine, and thiophenecarboxylic acid hydrazide, together with a bismuth tartarate complex as a catalyst, are useful indicator dyes in the method and composition of the present invention.

In general, in the dry phase assay for fructosamines, the indicator reagent composition is present in the carrier matrix in a sufficient amount to allow the visual or instrumental detection and measurement of a color transition. Usually, an indicator dye concentration in the indicator reagent composition incorporated into the carrier matrix in the range of about 1 mM to about 20 mM is sufficient to provide a detectable and differentiable color transition, either visually or by instrument, and to eliminate or minimize assay interference through indicator dye interaction with non-fructosamine test sample components. To achieve the full advantage of the present invention, the indicator dye concentration in the indicator reagent composition is in the range of from about 5 mM to about 15 mM. The particular amount of indicator dye, or combination of indicator dyes, present in the indicator reagent composition depends upon a variety of parameters, including the intensity of the indicator dye color transition and ability of the indicator dye to interact with fructosamines.

In addition to the indicator dye, the indicator reagent composition includes a buffer that maintains the indicator reagent composition at a sufficiently high pH to convert the fructosamine from its ketoamine form to its reducing, eneaminol form. A sufficiently high pH, such as from about 11 to about 13, and preferably from about 11 to about 12.5, assures that upon contact of the indicator reagent composition with the test sample, the fructosamine present in test sample is in its reactive eneaminol form. It is this reactive eneaminol-form of the fructosamine that interacts with the indicator dye to produce a color transition that can be correlated to the fructosamine concentration of the test sample.

It has been found that the sodium carbonate/sodium bicarbonate buffer, used in the prior art wet phase assay for fructosamines to provide a buffered pH of from about 10 to about 11, is unsuitable for use in an indicator reagent composition that is incorporated into a carrier matrix of a dry phase test strip. It has been theorized that the sodium carbonate/sodium bicarbonate buffer is unsuitable in a dry phase test strip of the present invention because the sodium bicarbonate precipitates during preparation of the test strip; pH changes occur at the surface that adversely affect the equilibrium reactions of the buffer ingredients; and/or the buffer ingredients decomposed during the drying procedures used in the manufacture of the test strips. Therefore, in accordance with the present invention, it has been found that for a dry phase test strip, a pH of from about 11 to about 13, and especially from about 11 to about 12.5, provides a sufficiently high pH for the indicator dye to react with the reactive eneaminol-form of the fructosamine. Accordingly, suitable buffers for the present invention include sodium hydrogen phosphate/sodium hydroxide, guanidine, potassium chloride/sodium hydroxide, methanolic sodium hydroxide, tetramethylammonium hydroxide, and other suitable buffers as are well known in the art; or combinations thereof.

The indicator reagent composition of the present invention also includes a reaction accelerator compound. The wet phase fructosamine assay disclosed by Baker required temperatures of about 37° C., or 98.6° F., in order for the reaction between the indicator dye and the fructosamine to proceed at a reasonable rate. However, the assay, even at this elevated temperature, required approximately 15 minutes to complete. Therefore, surprisingly and unexpectedly, it has been found that, by including a reaction accelerator compound in the indicator reagent composition, an assay for fructosamines can be conducted at room temperature with a dry phase test strip to yield fructosamine concentrations in as short a time as about three minutes. Therefore, the manipulative step of incubation of the test strip to accelerate the reaction is avoided. As a result, the dry phase test strip assay for fructosamines can be more easily and economically performed, an exceptional advantage for assays conducted at home.

Suitable reaction accelerator compounds that allow the assay to proceed at a reasonable rate at room temperature and that do not adversely affect assay sensitivity generally include nonionic surfactants and organic solvents, or combinations thereof. In general, anionic surfactants, such as sodium dodecylsulfate, sodium bis(2-ethylhexyl)sulfosuccinate, ammonium perfluoroalkyl sulfonates, and potassium fluorinated alkyl carboxylates, are not suitable reaction accelerator compounds because the indicator dyes and the reduced forms of the indicator dyes are not sufficiently solubilized by anionic surfactants. It should be noted that the reaction accelerator compounds also allow the fast and accurate fructosamine assay at room temperature in a wet phase assay procedure.

Nonionic surfactants found useful in the method and composition of the present invention are water-soluble or water-dispersible nonionic surfactants. However, water-insoluble nonionic surfactants also have provided a sufficiently rapid color response when used as the reaction accelerator compound in the composition of the present invention. To achieve the full advantage of the present invention, a nonionic surfactant, either water soluble or water insoluble, that is capable of solubilizing both the indicator dye, i.e., the tetrazolium salt, and the reduced form of the indicator dye, i.e., the formazan, is used as the reaction accelerator compound. One suitable class of nonionic surfactants is the ethoxylated and/or propoxylated octylphenols or nonylphenols containing from about 4 moles to about 100 moles, and preferably from about 6 moles to about 30 moles, of ethylene oxide or propylene oxide. Exemplary nonionic surfactants within this class are commercially available under the brand name TRITON, such as TRITON X-45, TRITON X-100 and TRITON N-111 from Rohm and Haas, Philadelphia, Pa. Similarly, ethoxylated or propoxylated fatty alcohols, including fatty alcohols containing from about 8 to about 20 carbon atoms and ethoxylated or propoxylated with from about 4 to about 100 moles of ethylene oxide or propylene oxide, can be used in the indicator reagent composition of the present invention. In addition, TRITON CF-32, an amine polyglycol condensate available commercially from Rohm and Haas, Philadelphia, Pa., is a suitable reaction accelerator compound.

Another nonionic surfactant that has been used as a reaction accelerator compound in the present invention is the ethoxylated acetylenic surfactant, 2,4,7,9-tetramethyl-5-decyn-4,7-diol containing from about 4 to about 30 moles of ethylene oxide, and commercially available under the brand names SURFYNOL 465, SURFYNOL 420 and SURFYNOL 485 from Air Products and Chemicals, Allentown, Pa. An additional class of suitable reaction accelerator compounds is the nonionic fluorinated alkyl polyoxyethylene ethanol surfactants, and available under the brand names FLUORAD FC-170-C and FLURORAD FC-171 available from 3M, St. Paul, Minn. Other nonionic surfactants that can be used as reaction accelerator compounds include, but are not limited to, polyethylene glycols, polypropylene glycols, glycerol esters, and ethoxylated or propoxylated fatty acids or fatty amides.

In addition, organic solvents, and especially aprotic organic solvents, such as dimethyl sulfoxide (DMSO), can be used alone, or in conjunction with a suitable nonionic surfactant, as the reaction accelerator compound. Other aprotic solvents that can be used as the reaction accelerator compound include dimethylformamide, hexamethylphosphoramide, and N-methyl pyrrolidone. In addition, certain protic organic solvents, such as hexanol and decanol, also have been used as the reaction accelerator compound.

Consequently, it is well within the experimental techniques of those skilled in the art of preparing test devices to design a dry phase quantitative assay of fructosamines in blood, serum and other liquid test samples by varying the relative amounts of test sample, and by varying the identity and amount of indicator dye, reaction accelerator compound and buffer, to provide detectable and differentiable color transitions, such that a comparison, either visually or by instrument, to color standards derived from standardized solutions of known fructosamine concentration is possible.

Therefore, in accordance with an important feature of the present invention, the color resolution achieved by using the indicator reagent composition of the present invention in a dry phase test strip permits detection of, and differentiation between, fructosamine concentrations of 0.5, 1.0, 1.5, 2.0, 2.5, 3.0, 3.5 and 4.0 mMol/L, and up, to about 6 mMol/L. Surprisingly and unexpectedly, the method and composition of the present invention allows the resolution and differentiation of fructosamine concentrations differing by as little as 0.5 mMol/L. In contrast to the prior art, the present dry phase assay method for fructosamines can be conducted at room temperature to yield fast and accurate assay results. Therefore, in accordance with the present invention, assay sensitivity is increased, especially at test sample fructosamine levels of between about 0.5 mMol/L and about 6 mMol/L, and especially between 1 mMol/L and 4 mMol/L, to ultimately yield more accurate and meaningful assay results.

To perform a dry phase assay for the fructosamine content of an aqueous test sample, the indicator reagent composition is produced first. For example, an indicator reagent composition is produced by dissolving 300 mg (0.79 millimole) of either tetrazolium violet or 600 mg (1.89 millimole) triphenyltetrazolium chloride in a 0.25 M aqueous sodium hydrogen phosphate/sodium hydroxide buffer (pH=12). Then 2 ml of a 20% by weight aqueous solution of polyvinylpyrrolidone polymer of approximate molecular weight 40,000; 1 ml of an ethoxylated nonylphenol containing about 10 moles of ethylene oxide; and 1 ml of dimethylsulfoxide was added to the aqueous solution of the indicator dye and the buffer. The resulting mixture was stirred until homogeneous. In the above example, the polyvinylpyrrolidone polymer is an optional ingredient added to enhance color uniformity, color intensity and color stability.

The indicator reagent composition then is incorporated into a suitable carrier matrix. After drying the impregnated carrier matrix, a test pad of the present invention results. Then, to determine the presence or concentration of fructosamines in a blood sample, the test pad contacts a blood sample, and the test pad undergoes a color transition due to an interaction between the fructosamines in the sample and the indicator reagent composition. If a visual assay detection is used, the resulting color then is compared to a color transition resulting from contacting a standard sample containing a known amount of fructosamine with a test pad. When the color of the test pad that contacted the standard fructosamine solution matches the color of the test pad that contacted the test sample, the concentration of fructosamines in the blood sample is revealed. If a more accurate instrumental assay detection is used, the color change of the test pad is determined by measuring the color transition intensity at a particular wavelength, then correlating this color transition intensity to the concentration of fructosamine in the test sample by comparison to the color transition intensity exhibited by solutions containing known concentration of fructosamines.

The dry phase, test pad assay for fructosamines that utilize the indicator reagent composition of the present invention is performed in accordance with methods well known in the art. As stated above, the assay for fructosamines is performed by contacting the blood, serum or other test sample with an analyte detection device that includes the indicator reagent composition. The analyte detection device can be dipped into the test sample, or the test sample can be applied to the analyte detection device dropwise. The resulting change in color of the analyte detection device demonstrates the presence of fructosamines; and, if so designed, the resulting color transition can be visually compared to a standardized color chart or can be determined spectrophotometrically to provide a quantitative measurement of the concentration of fructosamine in the blood, serum or test sample.

Typically, the analyte detection device is a reagent impregnated test strip, designed either as a single pad test strip (to assay only for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move, in response to capillary forces, through the matrix to contact the indicator reagent composition and produce a detectable and measurable color transition.

The carrier matrix can be any substance capable of incorporating the chemical reagents required to perform the assay of interest, as long as the carrier matrix is substantially inert with respect to the chemical reagents, and is porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occuring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and non-absorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix must include a hydrophilic or absorptive material. The handle usually is formed from hydrophobic materials such as cellulose acetate, polyethylene, terephthalate, polycarbonate or polystyrene, and the carrier matrix is most advantageously constructed from bibulous filter paper or nonbibulous polymeric films.

Therefore, in accordance with the method of the present invention, to perform a dry phase, test strip assay for fructosamines, a suitably buffered aqueous solution, including from about 1 mM to about 20 mM concentration of the indicator dye, first is prepared. A carrier matrix, such as a bibulous matrix, like filter paper, or such as a nonbibulous matrix, like a polyurethane membrane, then is saturated and impregnated with the aqueous indicator reagent composition either by spreading, by immersing or by spraying the aqueous indicator reagent composition onto sheets or precut strips of the filter paper. After removing the aqueous solvent by oven drying in an air oven at about 60° C. for about 10 to 20 minutes, the filter paper impregnated with the indicator reagent composition is cut to an appropriate size, such as a pad having dimensions from about 0.25 cm by about 0.5 cm to about 0.5 cm by about 1.0 cm. Alternatively, it is possible to separate the ingredients of the indicator reagent composition into two impregnating solutions and perform a two-dip impregnation procedure. The single dip procedure is especially recommended because only one solution is prepared, only one impregnation and drying step is required, and the leaching of ingredients incorporated into the carrier matrix during the first impregnation step into the second impregnation solution is precluded.

The filter paper impregnated with the indicator reagent composition then is secured to an opaque or transparent hydrophobic plastic handle with double sided adhesive tape. The resulting test strip then was dipped into a blood, serum, or other test sample for a sufficient time to saturate the test pad with the sample. After waiting a predetermined time, such as from about 3 minutes to about 5 minutes, the test strip is examined, either visually or by instrument, for a response. The color transition, if any, of the test pad reveals the presence or concentration of fructosamine in the blood, serum or other test sample. Fructosamine reduction of the indicator dye takes a longer time than fructosamine reduction of other substances. Therefore, in order to obtain the most accurate fructosamine assay, at least about 3 minutes, and preferably about 5 minutes, should pass before examining the test strip for a response.

As described above, it is well within the experimental techniques of those skilled in the art of preparing test devices to determine the proper balance between size of reagent pad, the strength of reagent impregnating solutions, the amount of test sample, and the method of introducing the test sample to the test strip, such as by pipetting rather than dipping, in order to design a quantitative assay for fructosamines utilizing the method and composition the present invention.

In many cases simple visual observation of the test strip provides the desired information. If more accurate information is required, a color chart bearing color spots corresponding to various known fructosamine concentrations, can be prepared for the particular indicator reagent composition used in the test strip. The resulting color of the test strip after contact with the blood or serum sample then can be compared with the color spots on the chart to determine the fructosamine concentration of the test sample.

If a still more accurate determination is required, a spectrophotometer or colorimeter can be used to more precisely determine the degree of color transition. In addition, the dry phase, reagent strip assay can be made quantitative by employing spectrophotometric or colorimetric techniques, as opposed to visual techniques, in order to more reliably and more accurately measure the degree of color transition, and therefore more accurately measure the concentration of fructosamines in the test sample.

As will be discussed more fully hereinafter, the ability to detect, differentiate between and measure concentrations of fructosamines in a test sample by employing a indicator reagent composition incorporated into a carrier matrix surprisingly and unexpectedly provides a diagnostic test to discover a glycemic condition and to determine glycemic control, efficacy of present therapy and patient compliance with the therapy. For example, a high concentration of fructosamines in the blood is a diagnostic indication that the patient suffers from diabetes mellitus, or that the prescribed therapy for diabetes either is insufficient or is not being followed. However, according to present day methods, the detection of fructosamines in blood requires a wet phase assay, at an elevated temperature, and an instrumental detection technique that is expensive and time-consuming. To date, dry phase test strips have not been used to assay for fructosamines because the reagents used to assay for fructosamines were found to be unstable under dry phase conditions and practically unreactive at room temperature in the solid phase. Surprisingly and unexpectedly, the method and composition of the present invention provide acceptable indicator reagent stability, reactivity and sensitivity to assay for fructosamines in a dry phase solid matrix. Accordingly, until the method of the present invention, no dry phase, test strip technique was available to accurately detect and measure the concentration of fructosamines in blood or serum.

Therefore, in accordance with an important feature of the present invention, it has been demonstrated that by impregnating the indicator reagent composition into a suitable carrier matrix, the presence and concentration of fructosamines in a blood sample can be achieved by using a dry phase test strip. As previously discussed, a dry phase test strip used for the assay of fructosamines in test samples generally includes a carrier matrix comprising an absorbent matrix that is amenable to treatment and impregnation with an indicator reagent composition; that permits the blood, serum or other test sample to permeate the carrier matrix rapidly enough to obtain fructosamine assays relatively quickly; and that does not contaminate the blood, serum or other liquid test sample either by test sample extraction of components comprising the carrier matrix or by appreciably altering the blood, serum or other test sample in a way to make the subsequent assays inconclusive, inaccurate or doubtful.

In accordance with one embodiment of the present invention, a test pad comprising a suitable carrier matrix impregnated with an indicator reagent composition was manufactured according to the one-step impregnation method outlined in Example 1.

EXAMPLE 1

To 50 mL of 0.25 M of sodium hydrogen phosphate/sodium hydroxide ($Na_2HPO_4$/NaOH) buffer (pH=12.0) was added 300 mg (0.79 millimoles) of tetrazolium violet, 2 mL of a 20% solution of polyvinylpyrrolidone polymer, 1.0 mL of an ethoxylated nonylphenol (TRITON X-100 available from Rohm and Haas, Philadelphia, Pa.) and 1.0 mL of dimethyl sulfoxide (DMSO). The resulting indicator reagent composition solution was impregnated onto WHATMAN 3MM filter paper, available from Whatman Ltd, Maidstone, Kent, U.K.. Finally, the impregnated filter paper was dried at 60° C. for 10 minutes to produce a test pad of the present invention.

Alternatively, the indicator reagent composition was impregnated into a urethane-based polymeric film, then dried. Similarly, an indicator reagent composition including 500 mg (1.58 millimoles) of triphenyltetrazolium chloride in place of the tetrazolium violet was impregnated onto a filter paper carrier matrix and dried. Nitroblue tetrazolium was found to be an unsuitable indicator dye because nitroblue tetrazolium was unstable at the pH of the indicator reagent composition of the present invention. In addition, the 0.25 M sodium hydrogen phosphate/sodium hydroxide buffer can be replaced with a 0.1 M guanidine buffer. However, a 0.1 M sodium carbonate/sodium bicarbonate buffer (pH=13.35) was found to be an unsuitable buffer upon incorporating the indicator reagent composition into the carrier matrix.

In accordance with another embodiment of the present invention, a test pad comprising a suitable carrier matrix impregnated with an indicator reagent composition was manufactured according to the two-step impregnation procedure outlined in Example 2.

EXAMPLE 2

WHATMAN 3MM filter paper, or alternatively a synthetic polymeric film, such as a permeable nylon, polyurethane, or polyvinylidene fluoride, was impregnated with an aqueous solution comprising 1% by weight TRITON X-100 ethoxylated nonylphenol and 1% by weight polyvinylpyrrolidone polymer, then dried for 10 minutes at 60° C. The dried carrier matrix then was impregnated with a 0.25 M $Na_2HPO_4$/NaOH buffer (pH=12) containing tetrazolium violet (8.6 mM) and 5% by weight polyvinylpyrrolidone polymer. After drying for 10 minutes at 60° C., a test pad of the present invention was produced. Similarly, the tetrazolium violet in the buffer solution can be replaced by 12 mM triphenyltetrazolium chloride in the second impregnation solution.

To demonstrate the new and unexpected results arising from incorporating the indicator reagent composition of the present invention into a dry phase test strip to detect and measure the amount of fructosamines in a test sample, fructosamine assays were performed on standardized fructosamine solutions. The results obtained from contacting standardized fructosamine solutions with dry phase test strips having a test pad comprising an indicator reagent composition impregnated into a carrier matrix are outlined below.

The color transitions resulting from contacting standardized fructosamine solutions with test pads incorporating an indicator reagent composition including either tetrazolium violet or triphenyltetrazolium chloride as the indicator dye were examined. Comparing the color transition resulting from contacting a test pad with a blood sample of unknown fructosamine concentration to the color transition resulting from contacting a test pad with a standardized fructosamine solution gives a quantitative assay for fructosamine concentration in the blood sample.

Figure 1:
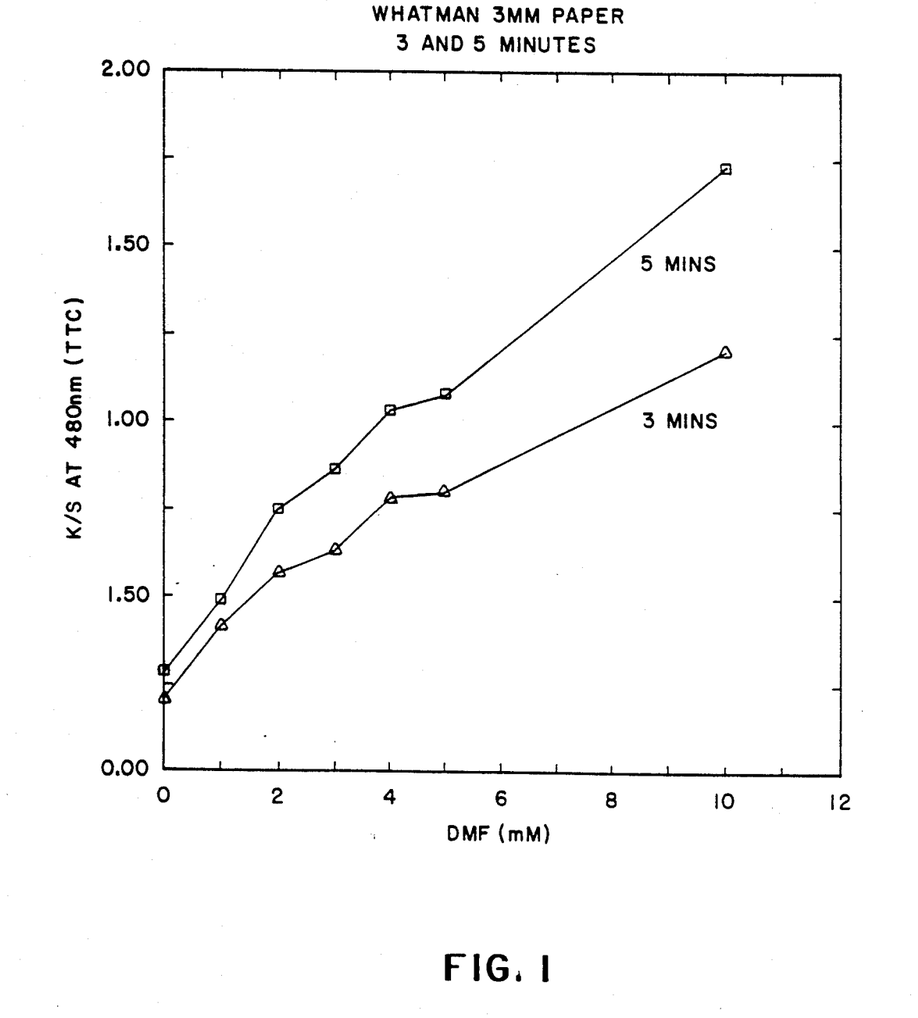
FIG. 1 is a plot of the Kubelka-Munk function (K/S) vs. concentration of 1-deoxy-1-morpholinofructose (DMF) utilizing a test device of the present invention incorporating triphenyltetrazolium chloride as the chromogenic indicator dye in the indicator reagent composition, wherein the test device is examined for a response both 3 minutes and 5 minutes after contacting the test device with the liquid test sample.
Figure 2:
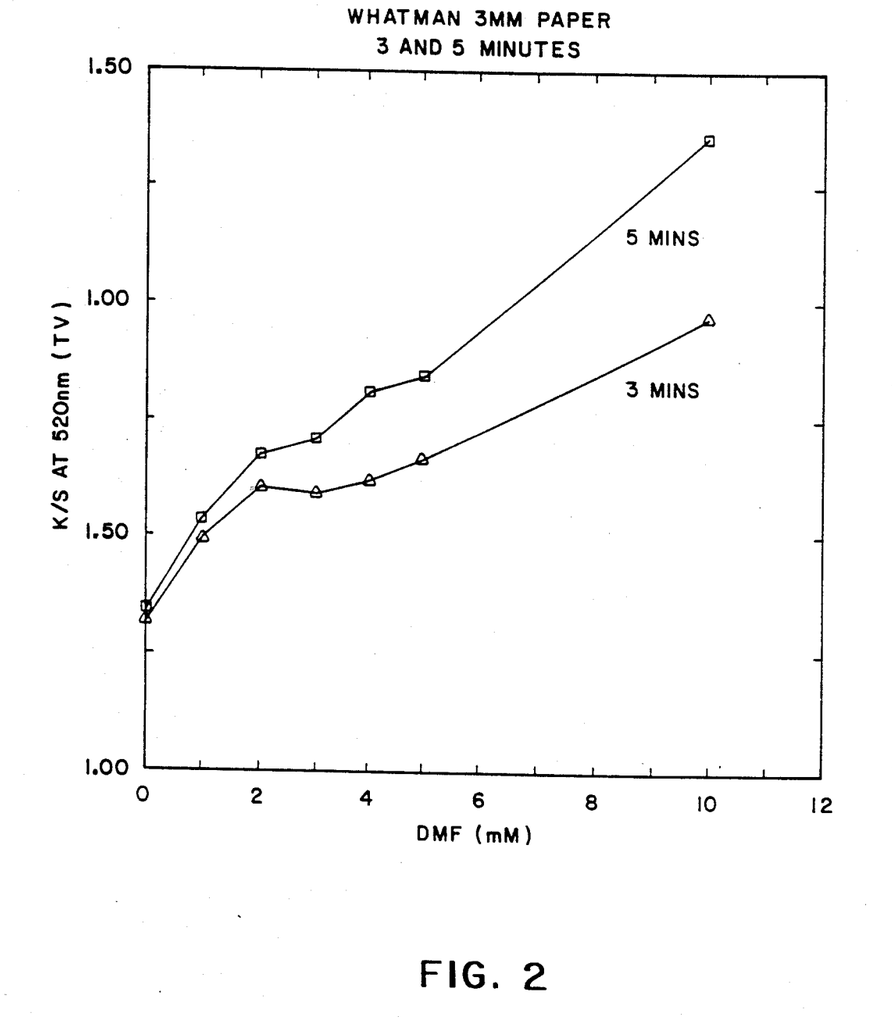
FIG. 2 is a plot of the Kubelka-Munk function (K/S) vs. concentration of 1-deoxy-1-morpholinofructose (DMF) utilizing a test device of the present invention incorporating tetrazolium violet as the indicator dye in indicator reagent composition, wherein the test device is examined for a response both 3 minutes and 5 minutes after contacting the test device with the liquid test sample.
Figure 3:
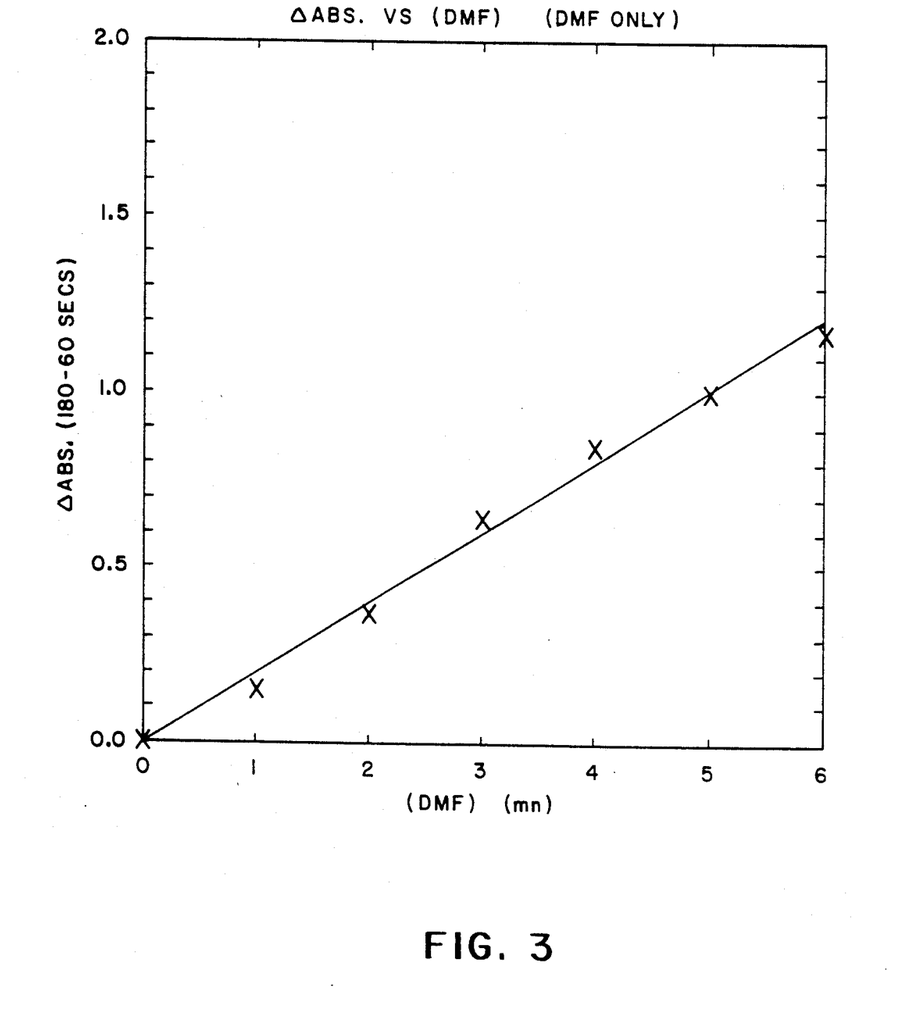
FIG. 3 is a plot of change of absorbance ($\Delta ABS$) vs. concentration of 1-deoxy-1-morpholinofructose (DMF) for absorbances measured 1 minute and 3 minutes after contacting the liquid test sample with a dry phase test strip of the present invention.

To show the new and unexpected results achieved by the composition and method of the present invention, assays for fructosamines were conducted using dry phase test strips comprising a test pad including either tetrazolium violet, that changes color from colorless to purple, or triphenyltetrazolium chloride, that changes color from colorless to pink-red, as the indicator dye of the indicator reagent composition. Dose response plots were graphed to demonstrate that the intensity of the color transition of the dye changed in direct proportion to the fructosamine concentration of the test sample. Individual assay results were determined by taking a reflectance measurement with a reflectance photometer approximately 3 minutes, and then approximately 5 minutes, after the test sample contacted the test strip. The reflectance measurements were taken at a wavelength of 480 nm (nanometers) for assays utilizing triphenyltetrazolium chloride as the indicator dye, and at a wavelength of 520 nm for assays utilizing tetrazolium violet as the indicator dye. The reflectance, as taken from the reflectance scale of zero to one, was incorporated into the Kubelka-Munk function:

$$K/S = (1-R)^2/2R,$$

wherein K is the absorption coefficient, S is the scattering coefficient and R is reflectance. The K/S values were plotted against the fructosamine concentration of the test sample. Generally, it can be stated that as reflectance decreases, the K/S value increases.

For example, FIG. 1 shows K/S values at 480 nm versus the 1-deoxy-1-morpholinofructose (DMF) fructosamine concentration of standardized solutions. Each test was run in duplicate, using two instruments. TABLE I tabulates the data plotted in FIG. 1, wherein the K/S value was determined both 3 minutes and 5 minutes after contacting the dry phase test strip of the present invention with a standardized solution of 1-deoxy-1-morpholinofructose (DMF), a synthetic fructosamine. The tabulated K/S values are given as duplicate pairs of the average K/S values for three replicate trials. The standard deviation over the replicate trials is approximately 0.1.

The data in TABLE I and the K/S vs. DMF concentration plot of FIG. 1 show that the concentration of fructosamines in various test samples can be differentiated by the dry phase test strip of the present invention.

TABLE I

K/S VERSUS CONCENTRATION OF DMF[1]

| DMF Concentration (mM)[2] of Standardized Solution | K/S at 480 nm | |
|---|---|---|
| | after 3 minutes | after 5 minutes |
| 0.0 | 0.25 | 0.28 |
| 1.0 | 0.46 | 0.49 |
| 2.0 | 0.57 | 0.75 |
| 3.0 | 0.63 | 0.80 |
| 4.0 | 0.79 | 1.04 |
| 5.0 | 0.80 | 1.05 |
| — | — | — |
| 10.0 | 1.21 | 1.74 |

[1]Test device included WHATMAN 3MM filter paper as the carrier matrix, and triphenyltetrazolium chloride as the chromogenic indicator dye (Example 1).
[2]mM is millimolar.

In assaying a test sample that does not include a fructosamine, i.e., DMF concentration is 0.0 mM, the K/S values at 480 nm, determined 3 minutes and 5 minutes after contact between the test device and the test sample, are almost identical (i.e., 0.25 and 0.28 respectively). The K/S values also are almost identical for a standardized solution including 1.0 mM DMF. However, for increasing fructosamine concentrations, up to 10 mM, and especially up to about 6 mM, the K/S values increased in direct proportion to the increasing fructosamine concentration for both the K/S values determined after 3 minutes and the K/S values determined after 5 minutes. Consequently, three minutes is a sufficient amount of time to allow an interaction between the indicator reagent composition and the fructosamine to occur, as demonstrated by the sufficient change in K/S values determined after a 3 minute interaction between the fructosamine solution and the indicator reagent composition. However, TABLE I and FIG. 1 also show that a 5 minute interaction time is preferable because the change in K/S values between succeeding levels of fructosamine concentrations (i.e., 1.0 mM vs. 2.0 ml DMF) is greater after 5 minutes than after 3 minutes, thereby giving a more accurate assay after a 5 minute interaction. No further improvements in assay accuracy were found by determining the K/S values at a time in excess of about 5 minutes.

Similarly, TABLE II tabulates the data plotted in FIG. 2. Again, the K/S values for a particular concentration of 1-deoxy-1-morpholinofructose was determined both 3 minutes and 5 minutes after contact of the dry phase test strip of the present invention with a standardized fructosamine solution The data of TABLE II and the plot of FIG. 2, obtained using tetrazolium violet as the indicator dye in an indicator reagent composition of the present invention, show essentially the same results as TABLE I and FIG. 1.

TABLE II

K/S VERSUS CONCENTRATION OF DMF[1]

| DMF Concentration (mM)[2] of Standardized Solution | K/S at 480 nm | |
|---|---|---|
| | after 3 minutes | after 5 minutes |
| 0.0 | 0.30 | 0.32 |
| 1.0 | 0.50 | 0.54 |
| 2.0 | 0.61 | 0.68 |
| 3.0 | 0.59 | 0.67 |
| 4.0 | 0.62 | 0.79 |
| 5.0 | 0.67 | 0.83 |
| — | — | — |
| 10.0 | 0.98 | 1.36 |

[1]Test device included WHATMAN 3MM filter paper as the carrier matrix, and tetrazolium violet as the indicator dye (Example 2).
[2]mM is millimolar.

Again the K/S values increased in direct proportion to the fructosamine concentration of the test sample over the fructosamine concentration range of 0 mM to 10 mM, and especially over the range of 0.5 mM to 6 mM. In addition, the K/S value can be determined 3 minutes after contact of the test sample with the test device of the present invention to provide accurate fructosamine assays. More accurate assays can be obtained if the K/S value is determined 5 minutes after contact between the test device and the test sample.

In accordance with an important feature of the present invention, the fructosamine concentration of a test sample including an unknown concentration of fructosamine can be found first by determining the K/S value at the appropriate wavelength for the indicator dye used in the assay at a time of at least 3 minutes after contact between the test device and the test sample. This K/S value then is used to find the fructosamine concentration of the test sample from a plot of K/S values vs. fructosamine concentration for standardized samples. It should be understood that the K/S values for the standardized sample and the test solution are determined by using the same indicator dye in the indicator reagent composition; by measuring the reflectance at the same wavelength; and by allowing the same amount of time to pass after the contact between the test device and the test sample before determining the K/S value; i.e., reflectance is measured after 3 minutes for all standardized samples and the test sample.

TABLE III and FIG. 3 show that the change of absorbance (ΔABS) that occurs from 1 minute to 3 minutes after contact between the test device and the test sample. FIG. 3 shows that the change of absorbance is essentially linear as the fructosamine concentration increases. Therefore, accurate fructosamine assays are achieved after a sufficient time elapses to allow the fructosamine in the test sample to interact with the indicator reagent composition.

TABLE III

DRY PHASE FRUCTOSAMINE ASSAY
Absorbance Change (ΔABS) for Different
Concentrations of 1-Deoxy-1-Morpholinofructose
(DMF) Using Tetrazolium Violet as the
Chromogenic Indicator Dye

| Concentration (mM) | Absorbance (1 to 3 Minutes) 524 nm | |
|---|---|---|
| | Without Albumin | With Albumin |
| 1.00 | 0.147 | 0.163 |
| 2.00 | 0.376 | 0.356 |
| 3.00 | 0.645 | 0.515 |
| 4.00 | 0.850 | 0.571 |
| 5 00 | 1.01 | 0.639 |

TABLE III-continued

DRY PHASE FRUCTOSAMINE ASSAY
Absorbance Change (ΔABS) for Different
Concentrations of 1-Deoxy-1-Morpholinofructose
(DMF) Using Tetrazolium Violet as the
Chromogenic Indicator Dye

| Concentration (mM) | Absorbance (1 to 3 Minutes) 524 nm | |
|---|---|---|
| | Without Albumin | With Albumin |
| 6.00 | 1.18 | 0.703 |

The specific amount of elapsed time is not necessarily important, however, the amount of elapsed time between test sample contact with the dry phase test strip and examination of the test strip for a response must be the same as the amount of time elapsed in the assay of the standardized solutions used to prepare the plot of K/S values vs. fructosamine concentration. From TABLE III, it is observed that when albumin is present in the test sample, i.e., the normal situation in assaying a blood sample, then the change in absorbance over time is decreased, thereby making the amount of time elapsed before examining the test strip for a response even less critical.

Overall, the data presented above shows that an indicator reagent composition of the present invention impregnated into a filter paper matrix, or into a polymeric film matrix, provides sufficient color resolution and assay sensitivity in the assay for the fructosamine content of a liquid test sample having fructosamine levels of between about 0.5 mMol/L and about 6 mMol/L. The method and composition of the present invention allow the visual differentiation of color transitions resulting from contact of the reagent-containing carrier matrix with a test sample containing fructosamines at levels of between about 0.5 mMol/L and about 6 mMol/L, and especially between about 1 mMol/L and about 4 mMol/L, thereby providing more accurate and trustworthy assays. The present invention further provides a method to quickly and accurately test for fructosamines in a test sample, at room temperature, by providing a test device and an indicator reagent composition of sufficient sensitivity to allow detection and measurement of low concentrations of fructosamines.

It has been demonstrated that color transitions resulting from samples having unequal fructosamine concentrations are sufficiently differentiable by using the indicator reagent composition of the present invention impregnated into a carrier matrix. These resolvable and differentiable color transitions are observed regardless of whether the carrier matrix is filter paper or a polymeric film. Therefore, employing the indicator reagent composition of the present invention in a suitable matrix demonstrates sufficient sensitivity to fructosamine concentrations to provide a simple dry phase test strip procedure to assay for fructosamines.

In accordance with an important feature of the present invention, more accurate and reliable assays for the fructosamine content in blood, serum and other liquid test samples can be performed by utilizing the indicator reagent composition of the present invention incorporated into a suitable carrier matrix. Investigations have shown that the glycosylation of serum proteins in chronic instances of hyperglycemia, i.e., diabetes mellitus, contributes to the secondary complications of diabetes, such as heart disease, retinopathy, kidney failure and microvascular disease. Thus, the measurement of glycated serum proteins has become an important diagnostic test to assess glycemic control, efficacy of therapy and patient compliance. The method and composition of the present invention provides sufficient color resolution of the assay and therefore sufficient assay sensitivity at fructosamine level from about 0.5 mMol/L to about 6 mMol/L; and especially from about 1 mMol/L to about 4 mMol/L. Furthermore, by performing the assay with a dry phase test strip, the simplicity and speed of the assay are significant improvements over prior art fructosamine assays.

In addition, the dry phase test strip of the present invention can indirectly provide a physician or an individual with the glucose concentration of a blood sample through the direct detection and measurement of the fructosamine concentration of the blood sample. For example, a blood sample can be assayed for fructosamine concentration by contacting the blood sample with a dry phase test strip of the present invention that includes a reagent test pad incorporating a reagent composition comprising a chromogenic indicator dye, a buffer and a reaction accelerator compound. The chromogenic indicator dye undergoes a color transition that, in intensity and degree, is directly proportional to the fructosamine concentration of the blood sample. Because the fructosamine concentration of a blood sample is directly proportional to the glucose concentration of the blood sample, a person skillful in the art can correlate the fructosamine concentration of the blood sample to the glucose concentration of the blood sample and therefore provide a color comparison chart for the fructosamine assay in glucose units. Overall, the results of the fructosamine assay are presented in glucose units because of the direct relationship of the degree and intensity of the color transition to amount of fructosamines in the sample, and because of the direct relationship between the amount of fructosamines in the sample to the amount of glucose in the sample.

Consequently, the physician or individual can perform an accurate and fast, indirect glucose assay of the blood sample through the direct assay for fructosamine concentration of the sample. Accordingly, the method and composition of the present invention allows the fast, accurate and trustworthy determination of the actual, time-averaged glucose concentration of blood, as opposed to the random determination of the apparent glucose concentration of the blood that varies with parameters such as diet, physical activities and medical treatments. Such a dry phase test strip procedure is both new and unexpected in the art.

Obviously, many modifications and variations of the invention as hereinbefore set forth can be made without departing from the spirit and scope thereof and therefore only such limitations should be imposed as are indicated by the appended claims.

We claim:

1. A composition capable of exhibiting a sufficient color transition upon contacting a fructosamine-containing liquid test sample to indicate the presence or concentration of fructosamine in the test sample comprising:
   (a) a chromogenic indicator dye capable of being reduced by a fructosamine;
   (b) a buffer to maintain the pH of the composition at a value of at least about 11; and
   (c) a reaction accelerator compound to enable the reaction between the fructosamine and the chromogenic indicator dye to proceed at ambient temperature.

2. The composition of claim 1 exhibiting a sufficient color transition within 5 minutes of contacting a fructosamine-containing liquid test sample to demonstrate the presence or concentration of fructosamine in the test sample.

3. The composition of claim 1 exhibiting a sufficient color transition within 3 minutes of contacting a fructosamine-containing liquid test sample to demonstrate the presence or concentration of fructosamine in the test sample.

4. A composition capable of exhibiting a sufficient color transition upon contacting a fructosamine-containing liquid test sample to indicate the presence or concentration of fructosamine in the test sample comprising:
  (a) a chromogenic indicator dye capable of being reduced by a fructosamine;
  (b) a buffer to maintain the pH of the composition at a value of at least about 11; and
  (c) a reaction accelerator compound capable of accelerating the reaction between the fructosamine and the chromogenic indicator dye selected from the group consisting of a nonionic surfactant, an organic solvent and combinations thereof.

5. The composition of claim 4 capable of exhibiting a sufficient color change upon contacting a fructosamine-containing liquid test sample including from about 0.5 mMol/L to about 6 mMol/L of fructosamine.

6. The composition of claim 4 capable of exhibiting a sufficient color change upon contacting a fructosamine-containing liquid test sample including from about 1 mMol/L to about 4 mMol/L of fructosamine.

7. The composition of claim 4 wherein the chromogenic indicator dye is present in an amount ranging from about 1 mM to about 20 mM.

8. The composition of claim 4 wherein the chromogenic indicator dye is present in an amount ranging from about 5 mM to about 15 mM.

9. The composition of claim 4 wherein the chromogenic indicator dye is selected from the group consisting of tetrazolium dyes, 2,6-dichlorophenol indophenol dyes and aroyl hydrazines.

10. The composition of claim 4 wherein the chromogenic indicator dye is selected from the group consisting of triphenyltetrazolium chloride, tetrazolium violet, blue tetrazolium, 3-(4,5-dimethyl-2-thiazolyl)-2,5-diphenyl-2H-tetrazolium bromide, p-dimethylaminobenzaldehyde coupled with acetylacetone, 2,6-dichlorophenol indophenol, 4-hydroxybenzoylhydrazine, 2-furoylhydrazine, nicotinoyl hydrazine, isonicotinyl hydrazine and thiophenecarboxylic acid hydrazide.

11. The composition of claim 4 wherein the buffer maintains the composition at a pH of from at least 11 to about 13.

12. The composition of claim 4 wherein the buffer maintains the composition at a pH of from at least 11 to about 12.5.

13. The composition of claim 4 wherein the buffer is selected from the group consisting of sodium hydrogen phosphate/sodium hydroxide, guanidine, potassium chloride/sodium hydroxide, methanolic sodium hydroxide, tetramethylammonium hydroxide and combinations thereof.

14. The composition of claim 4 wherein the nonionic surfactant selected from the group consisting of an amine polyglycol condensate, a 2,4,7,9-tetramethyl-5-decyn-4,7-diol containing from about 4 to about 30 moles of ethylene oxide, a fluorinated alkyl polyoxyethylene ethanol, a polyethylene glycol, a polypropylene glycol, a glycerol ester and combinations thereof.

15. The composition of claim 4 wherein the organic solvent selected from the group consisting of hexanol, decanol and a combination thereof.

16. The composition of claim 4 exhibiting a sufficient color transition within 5 minutes of contacting a fructosamine-containing liquid test sample at ambient temperature to demonstrate the presence or concentration of fructosamine in the test sample.

17. The composition of claim 4 exhibiting a sufficient color transition within 3 minutes of contacting a fructosamine-containing liquid test sample at ambient temperature to demonstrate the presence or concentration of fructosamine in the test sample.

18. The composition of claim 4 wherein the organic solvent is an aprotic organic solvent.

19. The composition of claim 18 wherein the aprotic organic solvent selected from the group consisting of dimethyl sulfoxide, dimethylformamide, hexamethylphosphoramide, N-methyl pyrrolidone and combinations thereof.

20. The composition of claim 4 wherein the nonionic surfactant is selected from the group consisting of an ethoxylated octylphenol, a propoxylated octylphenol, an ethoxylated nonylphenol, a propoxylated nonylphenol, an ethoxylated fatty alcohol, a propoxylated fatty alcohol, an ethoxylated fatty acid, a propoxylated fatty acid, an ethoxylated fatty amide, a propoxylated fatty amide, and combinations thereof.

21. The composition of claim 20 wherein the nonionic surfactant is ethoxylated with from about 4 moles to about 100 moles of ethylene oxide or is propoxylated with from about 4 moles to about 100 moles of propylene oxide, or combinations thereof.

22. The composition of claim 20 wherein the nonionic surfactant is ethoxylated with from about 6 moles to about 30 moles of ethylene oxide or is propoxylated with from about 6 moles to about 30 moles of propylene oxide, or combinations thereof.

23. A method of determining the presence or concentration of fructosamines in a liquid test sample comprising:
  (a) contacting the liquid test sample with a composition comprising a chromogenic indicator dye capable of being reduced by a fructosamine, a buffer to maintain the pH of the composition at a value of at least about 11, and a reaction accelerator compound capable of accelerating the reaction between the fructosamine and the chromogenic indicator dye selected from the group consisting of a nonionic surfactant, an organic solvent and combinations thereof; and
  (b) determining the presence or concentration of fructosamines in the liquid test sample from the intensity or degree of color change of the composition.

24. The method of claim 23 wherein the intensity or degree of color change is determined visually or instrumentally.

25. The method of claim 23 wherein the presence or concentration of fructosamines is determined at ambient temperature.

26. The method of claim 23 wherein the intensity or degree of the color change of the composition within 5 minutes after the liquid test sample contacts the composition is sufficient to accurately determine the presence or concentration of fructosamine in the liquid test sample.

27. The method of claim 23 wherein the intensity or degree of the color change of the composition within 3 minutes after the liquid test sample contacts the composition is sufficient to accurately determine the presence or concentration of fructosamine in the liquid test sample.

28. The method of claim 23 wherein the liquid test sample is a biological sample.

29. The method of claim 28 wherein the biological sample is whole blood or serum.

30. A method of determining the presence or concentration of fructosamines in a liquid sample comprising:
    (a) contacting the liquid sample with an analyte detection device comprising a reagent test pad including a composition comprising a chromogenic indicator dye capable of being reduced by a fructosamine, a buffer to maintain the pH of the composition at a value of at least about 11, and a reaction accelerator compound capable of accelerating the reaction between the fructosamine and the chromogenic indicator dye selected from the group consisting of a nonionic surfactant, an organic solvent and combinations thereof; and
    (b) examining the analyte detection device for a color transition in response to the fructosamine content of the liquid sample.

31. A method of detecting and measuring glucose in a test sample comprising:
    (a) contacting the test sample with a reagent composition comprising a chromogenic indicator dye capable of being reduced by a fructosamine, a buffer to maintain the pH of the composition at a value of at least about 11, and a reaction accelerator compound capable of accelerating the reaction between the fructosamine and the chromogenic indicator dye selected from the group consisting of a nonionic surfactant, an organic solvent and combinations thereof;
    (b) detecting and measuring the amount of fructosamines in the test sample from the intensity or degree of color change of the reagent composition; and
    (c) correlating the amount of fructosamines in the test sample to the amount of glucose in the test sample.

32. The method of claim 31 wherein the test sample includes from about 0.5 mM/L to about 6 mM/L of fructosamines.

33. The method of claim 31 wherein the test sample includes from about 1 mM/L to about 4 mM/L of fructosamines.

34. The method of claim 31 wherein the test sample is a biological sample.

35. The method of claim 34 wherein the biological sample is whole blood or serum.

36. A method of detecting diabetes mellitus by determining the concentration of glucose in a blood sample comprising:
    (a) contacting the blood sample with an analyte detection device comprising a reagent test pad including a reagent composition comprising a chromogenic indicator dye capable of being reduced by a fructosamine, a buffer to maintain the pH of the composition at a value of at least about 11, and a reaction accelerator compound capable of accelerating the reaction between the fructosamine and the chromogenic indicator dye selected from the group consisting of a nonionic surfactant, an organic solvent and combinations thereof;
    (b) examining the analyte detection device for a color transition in response to a fructosamine concentration of the blood sample;
    (c) determining the fructosamine concentration of the blood sample from the intensity or degree of the color transition; and
    (d) correlating the fructosamine concentration of the blood sample to the glucose concentration of the blood sample.

37. An analyte detection device to determine the presence or concentration of fructosamine in a liquid test sample comprising:
    a support strip;
    a reagent test pad; and
    a reagent composition incorporated into the reagent test pad, said reagent composition comprising
    (a) a chromogenic indicator dye capable of being reduced by a fructosamine to undergo a color transition;
    (b) a buffer to maintain the pH of the composition at a value of at least about 11; and
    (c) a reaction accelerator compound to enable the reaction between the fructosamine and the chromogenic indicator dye to proceed at ambient temperature.

38. The analyte detection device of claim 37 wherein the reaction accelerator compound is selected from the group consisting of a nonionic surfactant, an organic solvent and combinations thereof.

39. An analyte detection device to determine the presence or concentration of glucose in a liquid test sample comprising:
    a support strip;
    a reagent test pad; and
    a reagent composition incorporated into the reagent test pad, said reagent composition comprising
    (a) a chromogenic indicator dye capable of being reduced by a fructosamine to undergo a color transition;
    (b) a buffer to maintain the pH of the composition at a value of at least about 11; and
    (c) a reaction accelerator compound capable of accelerating the reaction between the fructosamine and the chromogenic indicator dye selected from the group consisting of a nonionic surfactant, an organic solvent and combinations thereof.

* * * * *